US008419688B2

(12) United States Patent
Woehr et al.

(10) Patent No.: US 8,419,688 B2
(45) Date of Patent: Apr. 16, 2013

(54) CATHETER ASSEMBLY AND COMPONENTS THEREOF

(75) Inventors: Kevin Woehr, Felsberg (DE); Michael Zerbes, Wabern (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 12/768,155

(22) Filed: Apr. 27, 2010

(65) Prior Publication Data
US 2010/0204675 A1 Aug. 12, 2010

Related U.S. Application Data

(63) Continuation of application No. 11/592,595, filed on Nov. 3, 2006.

(51) Int. Cl.
*A61M 5/178* (2006.01)

(52) U.S. Cl.
USPC ............ 604/167.01; 604/164.08; 604/167.02; 604/167.03; 604/167.04; 604/508; 604/264; 604/272

(58) Field of Classification Search ............ 604/164.08, 604/167.01, 167.02, 167.03, 167.04, 508, 604/264, 272
See application file for complete search history.

(56) References Cited

U.S. PATENT DOCUMENTS

| 3,416,567 A | 12/1968 | Dardel et al. |
| 3,585,996 A | 6/1971 | Reynolds et al. |
| 4,387,879 A | 6/1983 | Tauschinski |
| 4,449,693 A | 5/1984 | Gereg |
| 4,512,766 A | 4/1985 | Vailancourt |
| 4,842,591 A | 6/1989 | Luther |
| 4,874,377 A | 10/1989 | Newgard et al. |
| 4,883,461 A | 11/1989 | Sawyer |
| 4,929,235 A | 5/1990 | Merry et al. |
| 4,935,010 A | 6/1990 | Cox et al. |
| 4,966,586 A | 10/1990 | Vaillancourt |
| 5,053,014 A | 10/1991 | Van Heugten |

(Continued)

FOREIGN PATENT DOCUMENTS

| CA | 2133053 A1 | 3/1995 |
| DE | 32 10 148 A1 | 9/1983 |

(Continued)

OTHER PUBLICATIONS

Patent Abstracts of Japan, entitled "Indwelling Puncture Needle With Wing Having Branching Part," Application No. 11-021665; Publication No. 2000-217925; Published Aug. 8, 2000; Applicant Hanako Medical KK (3 pages).

(Continued)

*Primary Examiner* — Nicholas Lucchesi
*Assistant Examiner* — Scott Medway
(74) *Attorney, Agent, or Firm* — Klein, O'Neill & Singh, LLP

(57) ABSTRACT

Catheter assemblies are generally discussed herein with particular discussions extended to catheter assemblies having a tip protector, a valve, a valve opener, and optionally a needle wiper. The valve opener is disposed inside a catheter hub and is configured to be pushed by an IV set luer connector to open a valve following successful catheterization to pass fluids or other solutions through the catheter. A tip protector is incorporated to block the needle tip and prevent the same from accidental needle stick. A wiper is optionally included to wipe blood deposits on the needle when the same is retracted from the catheter.

20 Claims, 10 Drawing Sheets

U.S. PATENT DOCUMENTS

| | | | |
|---|---|---|---|
| 5,084,023 A | 1/1992 | Lemieux |
| 5,098,405 A | 3/1992 | Peterson et al. |
| 5,154,703 A | 10/1992 | Bonaldo |
| 5,188,607 A | 2/1993 | Wu |
| 5,195,980 A | 3/1993 | Catlin |
| 5,215,528 A | 6/1993 | Purdy et al. |
| 5,234,410 A | 8/1993 | Graham et al. |
| 5,269,771 A | 12/1993 | Thomas et al. |
| 5,334,159 A | 8/1994 | Turkel |
| 5,352,205 A | 10/1994 | Dales et al. |
| 5,405,323 A | 4/1995 | Rogers et al. |
| 5,454,790 A | 10/1995 | Dubrul |
| 5,562,630 A | 10/1996 | Nichols |
| 5,613,954 A | 3/1997 | Nelson et al. |
| 5,634,913 A | 6/1997 | Stinger |
| 5,651,772 A | 7/1997 | Arnett |
| 5,725,503 A | 3/1998 | Arnett |
| 5,738,144 A | 4/1998 | Rogers |
| 5,749,857 A | 5/1998 | Cuppy |
| 5,779,681 A | 7/1998 | Bonn |
| D397,434 S | 8/1998 | Pike |
| 5,817,069 A | 10/1998 | Arnett |
| 5,851,196 A | 12/1998 | Arnett |
| 5,865,806 A | 2/1999 | Howell |
| 5,911,705 A | 6/1999 | Howell |
| 5,911,710 A | 6/1999 | Barry et al. |
| 5,954,698 A | 9/1999 | Pike |
| 5,967,490 A | 10/1999 | Pike |
| 6,077,244 A | 6/2000 | Botich et al. |
| 6,080,137 A | 6/2000 | Pike |
| 6,171,287 B1 | 1/2001 | Lynn et al. |
| 6,352,520 B1 | 3/2002 | Miyazaki |
| 6,379,372 B1 | 4/2002 | Dehdashtian et al. |
| 6,506,181 B2 | 1/2003 | Meng et al. |
| 6,616,630 B1 | 9/2003 | Woehr et al. |
| 6,958,055 B2 | 10/2005 | Donnan et al. |
| 7,125,396 B2 | 10/2006 | Leinsing et al. |
| 7,470,254 B2 | 12/2008 | Basta et al. |
| 7,500,965 B2 | 3/2009 | Menzi et al. |
| 7,736,339 B2 | 6/2010 | Woehr |
| 2002/0128604 A1 | 9/2002 | Nakajima |
| 2004/0044313 A1 | 3/2004 | Nakajima |
| 2004/0243061 A1 | 12/2004 | McGurk |

FOREIGN PATENT DOCUMENTS

| | | |
|---|---|---|
| DE | 3303073 C1 | 9/1984 |
| DE | 44 34 569 A1 | 3/1995 |
| DE | 4434569 A1 | 3/1995 |
| DE | 201 04 539 U1 | 1/2002 |
| DE | 202 10 394 U1 | 9/2002 |
| EP | 0224641 A1 | 7/1986 |
| EP | 0370997 A2 | 11/1989 |
| EP | 0 408 290 A2 | 1/1991 |
| EP | 0 434 324 A1 | 6/1991 |
| EP | 0449510 A2 | 10/1991 |
| EP | 0497576 A1 | 8/1992 |
| EP | 0 554 841 A1 | 8/1993 |
| EP | 0 747 084 A2 | 12/1996 |
| EP | 0 799 626 A1 | 10/1997 |
| EP | 0875262 A2 | 11/1998 |
| EP | 0968736 A1 | 1/2000 |
| EP | 1 101 508 A2 | 5/2001 |
| EP | 1 101 508 A3 | 8/2001 |
| EP | 1 240 916 B1 | 9/2002 |
| EP | 1 374 942 A | 1/2004 |
| EP | 1 374 942 B1 | 1/2004 |
| EP | 1 421 969 A1 | 5/2004 |
| GB | 2 118 440 A | 11/1983 |
| WO | WO 92/13584 A1 | 8/1992 |
| WO | WO 96/40359 A1 | 12/1996 |
| WO | WO 97/45151 | 12/1997 |
| WO | WO 98/30268 A1 | 7/1998 |
| WO | WO 98/53875 | 12/1998 |
| WO | WO 99/08742 A1 | 2/1999 |
| WO | WO 99/26682 | 6/1999 |
| WO | WO 03/011381 A1 | 2/2003 |

OTHER PUBLICATIONS

Patent Abstracts of Japan, entitled "Safe Indwelling Needle," Application No. 2000-078335; Publication No. 2001-259029; Published Sep. 25, 2001; Applicant Medikit KK (7 pages).

Patent Abstracts of Japan, entitled "Safe Indwelling Needle," Application No. 2000-182911; Publication No. 2002-000727; Published Jan. 8, 2002; Applicant Medikit KK (4 pages).

Patent Abstracts of Japan, entitled "Indwelling Needle Structure," Application No. 2001-363865; Publication No. 2003-175112; Published Jun. 24, 2003; Applicant Mitsubishi Pencil Co Ltd (5 pages).

Patent Abstracts of Japan, entitled "Indwelling Needle Structure and Seal Material Used Therefor," Application No. 2005-035112; Publication No. 2005-261938 A; Published Sep. 29, 2005; Applicant JMS Co Ltd (5 pages).

Patent Abstracts of Japan, entitled "Indwelling Needle," Application No. 2004-143931; Publication No. 2005-323762; Published Nov. 24, 2005; Applicant Medikit KK (4 pages).

Patent Abstracts of Japan, entitled "Indwelling Needle," Application No. JP 1996-0040652; Publication No. JP 9206375; Published Aug. 12, 1997; Applicant Togo Medikit KK (2 pages).

Office Action mailed Sep. 16, 2008 from related U.S. Appl. No. 11/592,595, filed Nov. 3, 2006.

Final Office Action mailed Jun. 16, 2009 from related U.S. Appl. No. 11/592,595, filed Nov. 3, 2006.

Office Action mailed Jan. 22, 2010 from related U.S. Appl. No. 11/592,595, filed Nov. 3, 2006.

Provisional U.S. Appl. No. 60/211,733 filed Jun. 15, 2000.

European Search report from related European Application No. 07 819 546.8 dated Jan. 23, 2012 (16 pages).

European Search report from related European Application No. 11 007 265.9 dated Jan. 20, 2012 (12 pages).

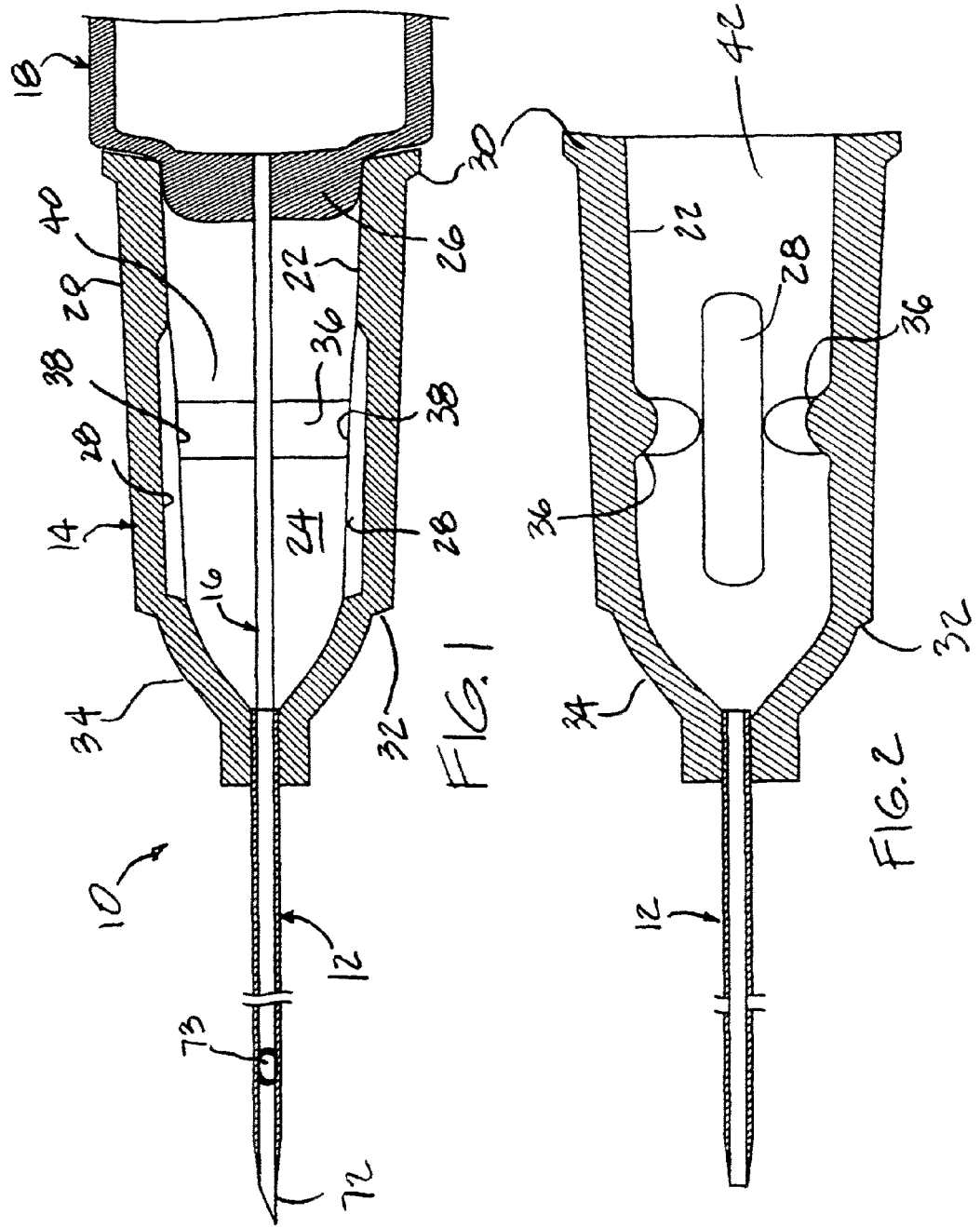

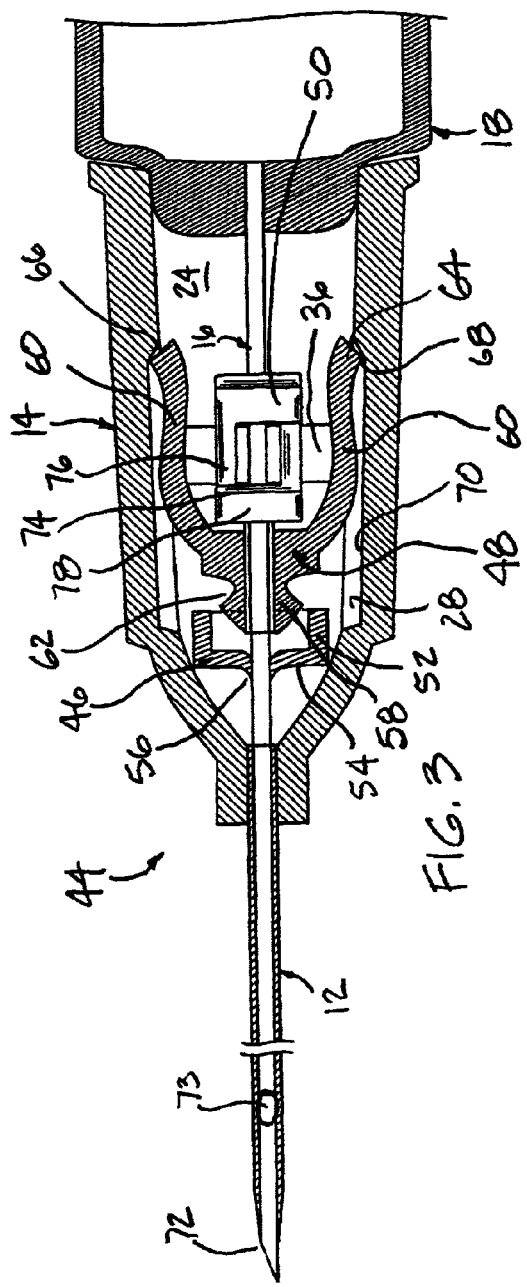
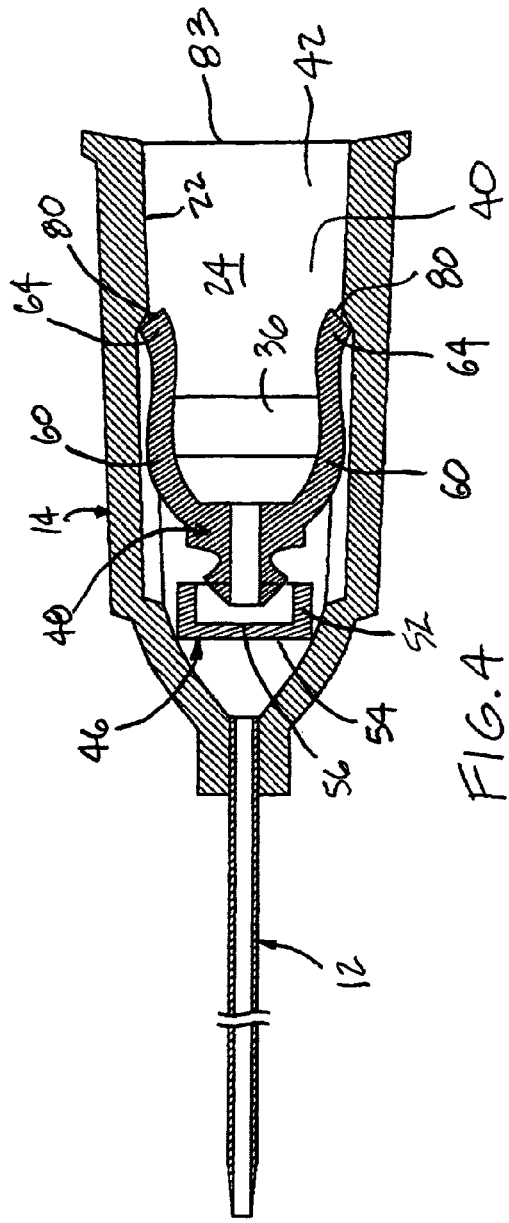

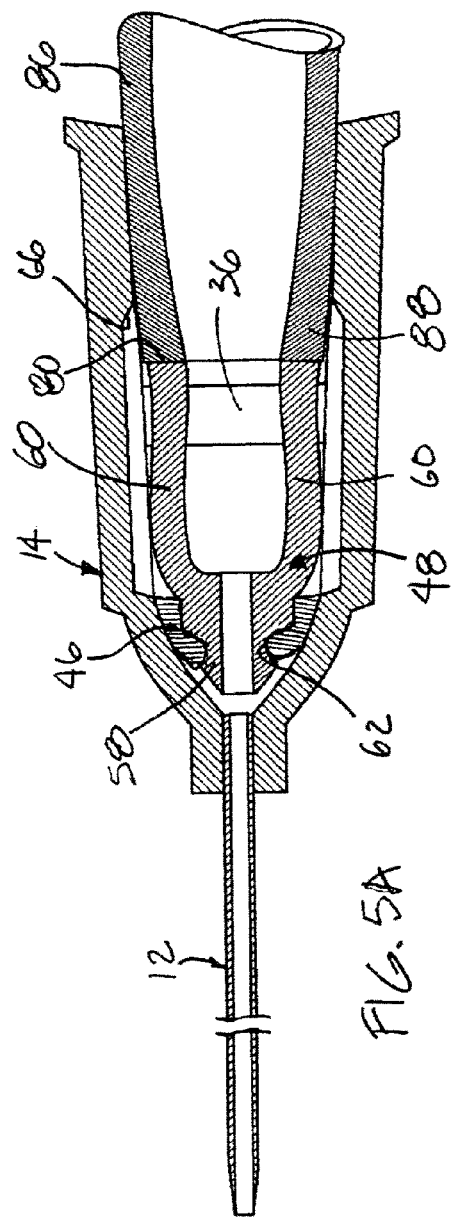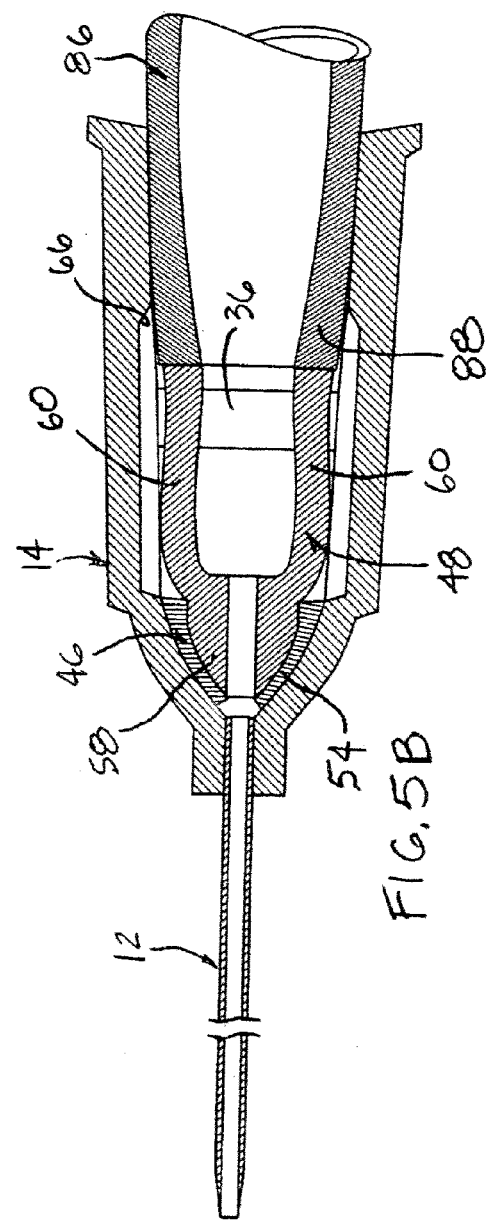

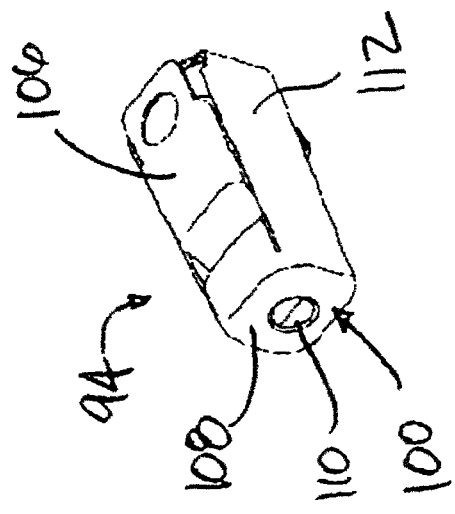
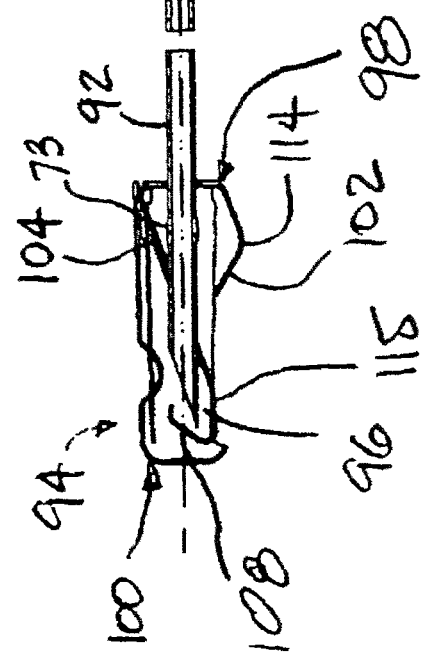
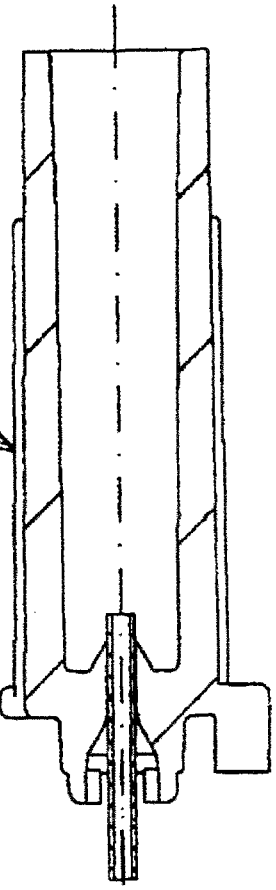

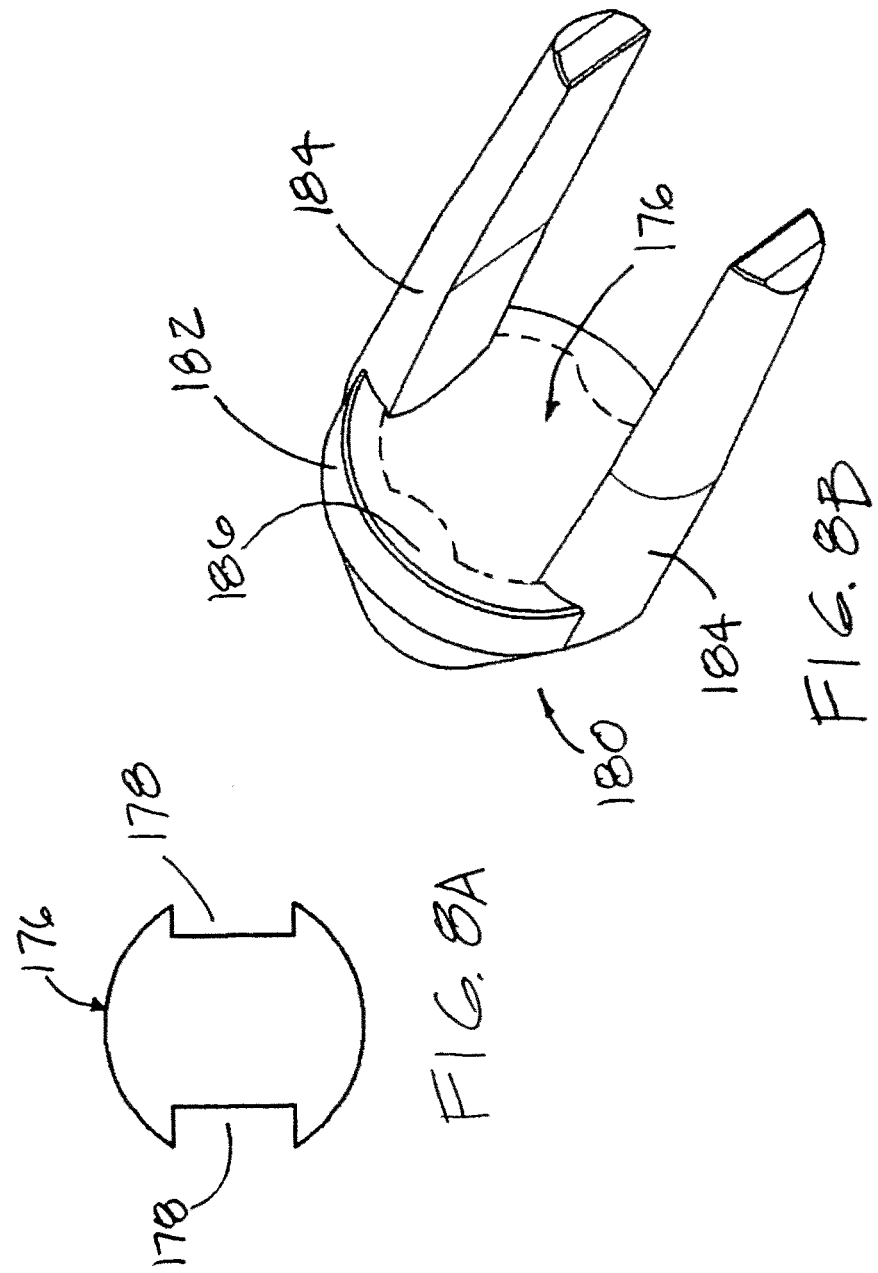

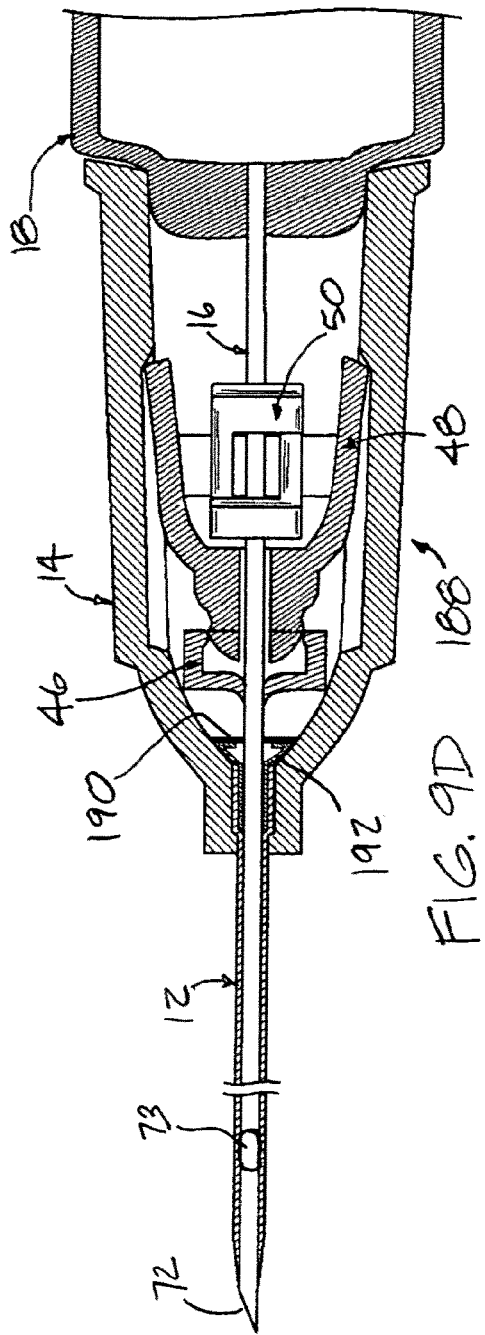
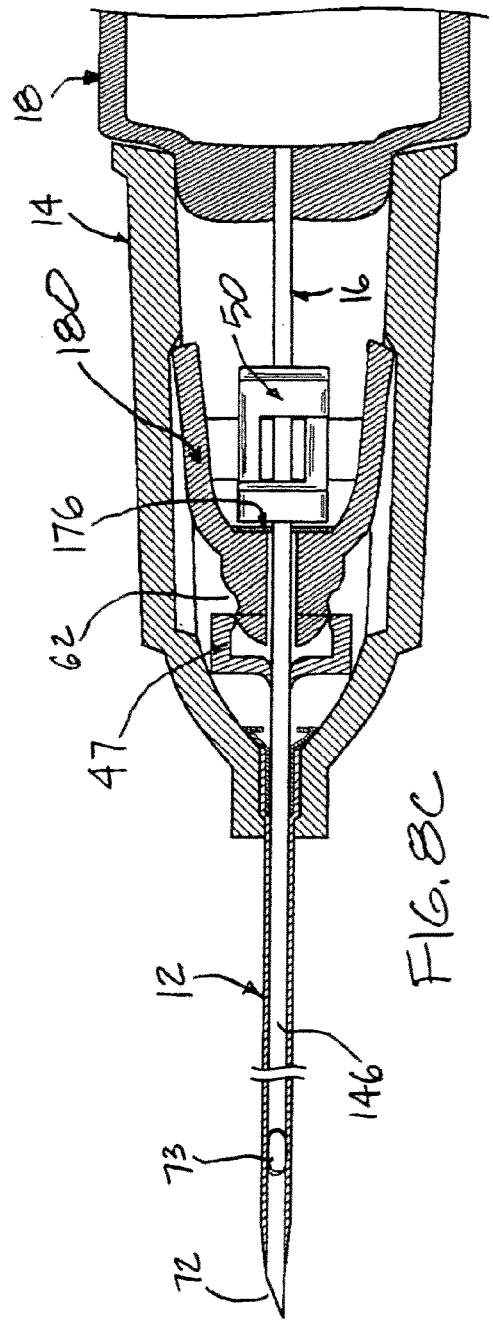

CATHETER ASSEMBLY AND COMPONENTS THEREOF

CROSS-REFERENCE TO RELATED APPLICATION

This application is a continuation of application Ser. No. 11/592,595, filed on Nov. 3, 2006, the entire contents of which are hereby expressly incorporated herein by reference.

TECHNICAL FIELD

Catheter assemblies are generally discussed herein with particular discussions extended to catheter assemblies having a tip protector, a valve, a valve opener, and optionally a needle wiper.

BACKGROUND

Insertion procedure for an IV catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to stop the flow of blood through the catheter; and (4) the healthcare worker then tapes the exposed end of the catheter (the catheter hub) to the patient's skin and connects it to the source of the fluid to be administered into the patient's vein.

The problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Other needle types similarly expose healthcare workers to risks of accidental needle sticks. For example, a doctor administering an injection, using a straight needle, a Huber needle, an epidural needle, etc., may place the used needle on a tray for subsequent disposal by a nurse. For the period between placing the used needle on a tray or a work station to the time it is discarded, the used needle is a potential source for disease transmissions for those that work near or around the needle.

Accordingly, all needles should be covered immediately following use to ensure greater worker safety. Ideally, the procedure for covering the needle tip should be passive, self activating, or at least simple to perform. In addition, the device for covering the needle should be reliable and robust.

More advantageously, a valve should be incorporated in the catheter assembly to minimize blood exposure following successful catherization. In addition, as blood comes in contact with the needle and is deposited on the needle, the needle assembly should further incorporate means for wiping the needle of the deposited blood upon retracting the needle.

SUMMARY

In accordance with aspects of the present invention, there is provided a catheter assembly comprising: a first hub comprising a housing comprising an exterior surface and an interior surface defining an interior cavity; a tube attached to the first hub and extending distally of the first hub; a second hub comprising a housing comprising an exterior surface and an interior surface defining an interior cavity; a needle having a needle tip attached to the second hub and projecting distally of the second hub and into the tube; a valve comprising a top surface, a skirt depending therefrom, and an opening on the top surface having the needle projecting therethrough; a valve opener comprising an actuating end, at least one leg extending proximally therefrom, and a wiper comprising a perimeter defining an opening and the needle in contact with the perimeter for wiping the needle as the needle is retracted away from the tube.

Other aspects of the present invention include a catheter assembly comprising: a) a catheter hub comprising a housing comprising an exterior surface and an interior surface defining an interior cavity; b) a catheter tube attached to the catheter hub and extending distally of the catheter hub; c) a needle hub comprising a housing; d) a needle having a needle tip attached to the needle hub and projecting distally of the needle hub and into the catheter tube; e) a valve for limiting blood backflow positioned in the interior cavity of the catheter hub; f) a valve opener for opening the valve positioned proximally of the valve; and g) a tip protector positioned adjacent the valve opener for blocking the needle tip, wherein the tip protector comprises: (1) a tip protector housing having an interior surface; (2) a first arm extending from a distal wall of the tip protector housing biased towards the interior surface of the catheter hub; (3) a second arm extending from a proximal wall of the tip protector housing biased towards the interior surface of the catheter hub; and (4) a third arm extending from the proximal wall of the tip protector housing biased against a side of the needle.

In accordance with other aspects of the present invention, there is provided a catheter assembly comprising: a catheter hub comprising a housing defining an interior cavity and having a catheter tube extending distally thereof; a needle hub comprising a housing defining an interior cavity and having a needle having a needle tip extending distally thereof; the needle projecting into the catheter tube; a hemostatic valve positioned within the interior cavity of the catheter hub having an opening; a valve opener positioned adjacent the hemostatic valve and comprising an actuating end comprising a cone section and a pair of legs defining a gap extending proximally thereof; a wiper having the needle passing therethrough for wiping the needle as the needle is retracted from the catheter tube; and wherein a tip protector comprising an arm and a wall comprising an opening and is positioned in the gap defined by the two legs.

In accordance with other aspects of the present invention, there is provided a method of wiping blood from a needle during a process of emplacing a catheter using a catheter assembly. The method comprises puncturing a person's vasculature with a sharp distal tip of the needle of the catheter assembly. The needle extends distally from a first hub including a housing having an exterior surface and an interior surface defining an interior cavity. The method further comprises penetrating the vasculature with the catheter of the catheter assembly. The catheter is disposed about the needle and extends distally from a second hub including a housing having an exterior surface and an interior surface defining an interior cavity. The first and second hubs releasably engage one another. The method further comprises withdrawing the needle from the vasculature while maintaining the catheter within the vasculature by disengaging the first hub from the second hub and moving the first hub proximally with respect to the second hub. The proximal movement causes the needle to withdraw from the catheter. The method further comprises wiping blood from the needle as it withdraws by passing the needle through a wiper. The wiper has a continuous perimeter defining an opening. The perimeter is in contact with the needle for wiping the needle.

In accordance with other aspects of the present invention, there is provided a method of cleaning an exterior of a needle during a process of emplacing a catheter using a catheter assembly. The method comprises inserting the needle of the catheter assembly into a person's vasculature at an access site. The needle extends distally from a proximal hub. The method further comprises inserting the catheter of the catheter assembly into the vasculature at the access site. The catheter is disposed about the needle and extends distally from a distal hub. The proximal and distal hubs releasably engage one another. The method further comprises disengaging the proximal hub from the distal hub and moving the proximal hub proximally with respect to the distal hub. The proximal movement draws the needle out of the vasculature and the catheter while the catheter remains within the vasculature. The method further comprises passing the needle through a wiper as it withdraws. The wiper removes blood from the exterior of the needle. The wiper has a continuous perimeter defining an opening. The perimeter is in contact with the exterior of the needle for wiping the needle.

Still yet in accordance with other aspects of the present invention include provisions for registering a pair of legs on the valve opener to the catheter hub by forming two axially extending undercut within the interior wall surface of the catheter hub for cooperating with the two legs.

In a preferred embodiment of the present invention, a raised bump or projection is formed within the interior cavity of the catheter hub for retaining a tip protector within the catheter hub during retraction of the needle hub away from the catheter hub.

In yet other aspects of the present invention, a wiper in the form of an O-ring is used to wipe the needle from blood deposits.

Other aspects and features of the catheter assemblies provided herein may be better appreciated as the same become better understood with reference to the specification, claims, and appended drawings.

BRIEF DESCRIPTION OF THE DRAWINGS

The appended drawings include:

FIG. 1 is a cross-sectional side view of a catheter assembly provided in accordance with aspects of the present invention;

FIG. 2 is a cross-sectional side view of the catheter of FIG. 1 with the needle and needle hub removed therefrom;

FIG. 3 is a partial cross-sectional side view of a safety catheter assembly provided in accordance with aspects of the present invention, which includes a valve, a valve opener, and a tip protector;

FIG. 4 is a partial cross-sectional side view of the safety catheter assembly of FIG. 3 with the needle hub, needle, and tip protector removed therefrom;

FIG. 5A is a cross-sectional side view of the catheter assembly of FIG. 4 with an IV set luer connector coupled to the catheter hub and pushing a valve opener distally into the valve;

FIG. 5B is a cross-sectional side view of an alternative catheter assembly, similar to the assembly of FIGS. 3-5A, wherein the valve opener does not incorporate barbs to permit disengagement with the valve upon retraction of the IV-set luer connector;

FIG. 6 is a cross-sectional side view of a needle hub and needle with a tip protector covering the needle tip;

FIG. 7 is a perspective view of the tip protector of FIG. 6;

FIG. 8A is a plan view of a wiper provided in accordance with aspects of the present invention, which includes two cut-outs;

FIG. 8B is a perspective view of a valve opener provided in accordance with aspects of the present invention having a wiper, according to FIG. 8A, attached to a proximally facing attachment surface;

FIG. 8C is a cross-sectional side view of a catheter assembly provided in a accordance with aspects of the present invention having the valve opener of FIG. 8B, including the wiper, positioned internally of the catheter hub;

FIG. 9D is a cross-sectional side view of a catheter assembly provided in a accordance with aspects of the present invention having a wiper positioned distally of a valve and valve opener;

DETAILED DESCRIPTION

Figure 9A:
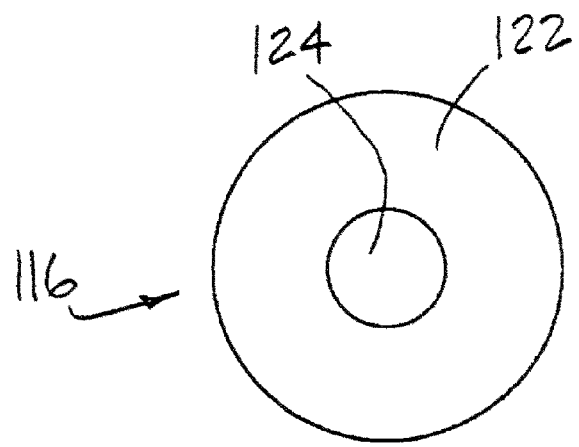
FIG. 9A is a plan view of a first alternative wiper provided in accordance with aspects of the present invention.

The detailed description set forth below in connection with the appended drawings is intended as a description of the presently preferred embodiments of a catheter assembly for use with valves and needle tip protectors provided in accordance with aspects of the present invention and is not intended to represent the only forms in which the present invention may be constructed or utilized. The description sets forth the features and the steps for constructing and using the catheter assembly of the present invention in connection with the illustrated embodiments. It is to be understood, however, that the same or equivalent functions and structures may be accomplished by different embodiments are also intended to be encompassed within the spirit and scope of the invention, especially those incorporating a combination of features shown in the different embodiments included herein. As denoted elsewhere herein, like element numbers are intended to indicate like or similar elements or features.

Referring now to FIG. 1, a partial cross-sectional side view of a catheter assembly provided in accordance with aspects of the present invention is shown, which is generally designated 10. The catheter assembly 10 comprises a catheter tube 12 attached to a catheter hub 14 having a needle 16, which is attached to a needle hub 18, projecting through the catheter tube 12 in a ready to use position. The needle 16 has a sharpened needle tip 72 and a crimp, bump, or clip engagement section 73. The catheter hub 14 comprises an exterior surface 20 and an interior surface defining an interior cavity 24. A needle hub nose section 26 preferably projects into the interior cavity 24 of the catheter hub 14 and a combination groove and projection (not shown) incorporated between the catheter hub 14 and needle hub 18 to fix relative angular rotation between the two.

In one exemplary embodiment, a pair of diametrically opposed channels 28 are formed in the interior wall surface 22 of the catheter huh 14. The channels 28 are formed as indentations in the interior wall surface 22 of the catheter hub and each has a length measured about 20% to about 85% of the length of the catheter hub, measured from the proximal threads 30 to the distal shoulder 32 adjacent a frusto-conical nose section 34. The channels 28 may be formed by known injection molding techniques.

In one exemplary embodiment, a pair of projections 36 are incorporated in the interior cavity 24 of the catheter hub 14. The two projections 36 are preferably symmetrical about the two channels 28 and each comprises two ends 38 that contact the two channels 28. In an alternative embodiment, the two ends 38 can be spaced apart from the two channels 28 and each projection 36 may be an indentation rather than a raised bump. Thus, in a preferred embodiment, the interior cavity 24 of the catheter hub, at the two projections or bumps 36, have a diameter measured from one bump to another bump, called a bump diameter, that is smaller than the diameter of the interior cavity of the catheter hub 14 measured from a point 40 adjacent the two bumps, called a bore diameter. Also at the two projection or bumps 36, the interior cavity 24 of the catheter hub 14 has a diameter measured from one channel 28 to another channel 28, called a mean channel diameter, that is larger than the bump diameter and the bore diameter 40.

FIG. 2 is a cross-section side view of the catheter hub 14 of FIG. 1 taken along a transverse plane and with the needle 16 and needle hub 18 removed therefrom. Although relative positions of the channel 28 to the hub 14 and of the bump 36 to the channel 28 are shown, they can each vary proximally towards the proximal opening 42 or distally towards the nose section 34 and relative to one another or in a rotation relative to the needle bevel 72 without deviating from the spirit and scope of the present invention.

Referring now to FIG. 3, a partial cross-sectional side-view of a safety IV catheter assembly provided in accordance with aspects of the present invention is shown, which is generally designated 44. In one exemplary embodiment, the catheter assembly 44 comprises a hemostatic valve 46, a valve opener 48, and a tip protector 50 positioned inside the interior cavity 24 of the catheter hub 14 of FIG. 1. The tip protector 50 may be the same as one of the many tip protectors shown and described in U.S. Pat. No. 6,616,630 to Woehr et al., the contents of which are expressly incorporated herein by reference as if set forth in full. The tip protector 50 is seated within the interior cavity 24 by moving the tip protector distally in the direction of the needle tip 72 until the two elbow sections 74 (only one shown) located between the two arms 76 and the two fingers or distal walls 78 (only one shown) move distally of the projection 36 inside the catheter hub. Alternatively, two recesses may be incorporated instead of the two bumps for interacting with the two elbow sections 74.

The hemostatic valve 46 may be made from a thermoplastic elastomer (TPE), such as polyisoprene or silicone rubber, and generally speaking comprises a skirt section 52 and a top 54 having a cut-out 56 comprising a plurality of slits, such as three slits resembling a three-sided star or a single slit, for expanding the cut-out when deflected. The hemostatic valve 46 is widely commercially available and is a well known component in the relevant art. In accordance with aspects of the present invention, a plurality of bumps, stretched ridges, or protuberances may be incorporated around the external circumference of the skirt section 52 for ensuring sufficient air flow between the valve skirt 52 and the inside surface 22 of the catheter hub for purposes of blood flashback. In yet other aspects of the present invention, the cut-out 56 is provided with a sufficient gap to permit air movement for purposes of blood flashback. In the latter alternative embodiment, an air tight seal is preferred between the exterior skirt section and the interior surface 22 of the catheter hub.

The valve opener 48 comprises an actuating end 58 and a pair of legs 60. In one exemplary embodiment, the actuating end 58 comprises a frusto-conical shape distal end configured to project against the top 54 of the valve 46, as further discussed below with reference to FIG. 5. In accordance with aspects of the present invention, the actuating end 58 comprises one or more undulating surfaces or barbs 62 for mating engagement with the cut-out 56 and plurality of slits on the hemostatic valve.

In one exemplary embodiment, the valve opener 48 is formed from a hard plastic material, which may be a polycarbonate material, a polyoximethylene material or the like. The two legs 60 are formed such that they spread radially outwardly relative to the needle shaft 16. In a specific aspect of the present invention, the two legs 60 are aligned with the two channels 28 and are registered to the two channels. The length and geometry of the valve opener 48 are such that the nose section 58 abuts the skirt section 52 of the valve 46 and the valve exerts a counter force pushing the two proximal ends 64 of the two legs 60 against the proximal ledge 66 of each respective channel 28 (See, e.g., FIG. 9D). The skirt section 52 is therefore under a slight compression caused by the nose section 58 of the valve opener 48 pushing against the skirt section. Alternatively, the nose section 58 may be spaced apart from and not contact the valve 46 in the ready to use position (FIG. 3).

The two legs 60 are preferably registered to the two channels 28 without a radial compression. In other words, the radial most tip 68 of each leg 60 is not biased against the wall surface 70 of the respective channel 28. However, a slight radial compression may be practiced without deviating from the spirit and scope of the present invention.

Referring now to FIG. 4, the safety IV catheter assembly of FIG. 3 is shown with the needle 16, tip protector 50, and needle hub 18 removed. In practice, this represents the position of the catheter following successful catheterization. As disclosed in the '630 Woehr et al. patent, when the needle 16 is withdrawn following catheterization, the tip protector 50 is withdrawn with the needle and remains with the needle to block the needle tip 72. In certain aspects of the present invention, a crimp, bump, or clip engagement section 73 is used to engage the opening on the tip protector 50 to secure the tip protector to the needle. U.S. patent application Ser. No. 11/496,769 to Kevin Woehr, entitled Needle Assembly and Components Thereof discloses a tip protector comprising side walls for surrounding the needle tip, which may be useable with the catheter assemblies provided in accordance with aspects of the present invention. The contents of the '769 application are expressly incorporated herein by reference. In yet other aspects of the present invention, the tip protector 50 incorporates an opening that cants over to grip the needle. Exemplary tip protectors that cant over to grip the needle are disclosed in U.S. Pat. No. 6,709,419 to Kevin Woehr, patent application Ser. No. 10/677,810 to Pat Latona, entitled Protective Needle Clips, and patent application Ser. No. 10/954,041 to Matthew Kohler, entitled Protective Clips. The contents of each of the foregoing references are expressly incorporated herein by reference.

As shown in FIG. 4, the top section 54 of the valve 46 recoils when no longer deflected by the needle and the cut-out 56 closes to form a seal. Thus, blood flow from the direction of the catheter tube 12 is stopped. Although not depicted, the exterior circumference of the valve 46 is wedged into the interior cavity and the valve is under compression by the interference fit. As the blood flow has been stopped, a health care worker can take his or her time in connecting an IV set luer connector to the catheter hub 14, fix the catheter hub with tape to the patient, and dispose of the used needle without excessive blood leakage through the catheter hub. Alternatively, the valve can provide a semi-permeable seal, which gives the health care worker ample time to make the required connections, fixations, and disposal of used needles before blood would exit the catheter hub 14 at the proximal end 42.

Assuming the opening 42 of the hub 14 defines a planar surface 83, in one exemplary embodiment, the end surface 80 of the two legs 60 at the two proximal ends 64 are positioned at an angle to the planar surface 83. The two legs 60 should also project radially inwardly of the nominal internal diameter of the catheter hub 14 at a position just proximal to the two proximal ends 64, i.e., the bore diameter 40. As further discussed below with reference to FIG. 5, the projection provides a contact surface on each proximal end 64 of the valve opener 48 for urging by a IV-set Luer connector. In an alternative embodiment, the end surfaces are generally parallel to the planar surface 83 defined by the opening 42.

FIG. 5A depicts an IV-set Luer connector 86 pushed into the opening 42 of the catheter hub 14. As the connector 86 is pushed distally forward, its distal end 88 abuts the two end surfaces 80 of the seal opener 48 and advances the opener 48 distally forward. The opener 48 in turn moves into the top area 54 of the seal and forces the cut-out 56 to deflect. The combination friction and barbs 62 on the actuating end 58 of the valve opener 48 allow the two to remain engaged. The valve 46 remains opened and fluid communication is provided between the catheter tube 12 and the interior cavity 24 of the catheter hub 14. Medicaments, IV solutions, or other fluids may now be introduced through the connector 86 and catheter 12. If the IV set luer connector 86 is subsequently withdrawn from the catheter hub 14, then the valve 46 would remain open and consequently there could be blood leakage. Alternatively, the actuating end 58 does not incorporate barbs 62 as shown in FIG. 5B thus allowing the top section 54 of the valve to separate from the actuating end 58. This allows the valve opener 48 to be moved proximally by action of the resilient top section while at the same time allows the cut-out to reseal itself.

FIG. 6 is a cross-sectional side view of a needle hub 90 having a needle 92 attached at end thereof and a tip protector 94 covering the needle tip 96. As known in the art, a flashback plug (not shown) is normally placed in the proximal end of the needle hub 90. The tip protector 94 is the same as that shown and described in application Ser. No. 11/496,769, which was previously incorporated herein by reference. As disclosed in the '769 application, the tip protector 94 comprises a first protector body 98 surrounded by a second protector body 100. The first protector body comprises a short arm 102 and a long arm 104, which both have portions that, at least in part, extend to one side of the centerline of the needle 92. The second protector body 100 (FIG. 7) partially surrounds the first protector body and comprises a deflector plate 106, a front wall 108 having an opening 110 and two side walls 112 (only one shown). When the tip protector 94 is in the protective position over the needle tip (FIG. 6), the needle tip is surrounded by the plurality of walls.

In one exemplary embodiment, the combination needle hub 90, needle 92, and tip protector 94 of FIG. 6 may be used with the catheter shown in FIG. 4. The projection 36 on the hub 14 would be positioned proximally relative to the apex 115 of the long arm 104 of the tip protector 94 to retain the tip protector 94 in the catheter hub 14. Alternatively, the projections 36 may be omitted and the arm 102 and deflector plate 106 resiliently engage the interior wall surface 22 to retain the tip protector 94 to the catheter hub.

Generally speaking, when a needle is withdrawn from a catheter tube following successful catheterization, residue blood may deposit on the needle shaft. The sight and presence of blood on a retracted needle are undesirable and potentially contagious. Thus, in accordance with aspects of the present invention, wipers are provided for wiping the needle upon retracting the same from a catheter. FIGS. 8A, 9A, 9B, and 9C are plan views of four different wipers 176, 116, 118 and 120 provided in accordance with aspects of the present invention. As further discussed below with reference to FIGS. 8B and 9D, the wipers are configured to be attached to a valve opener or a catheter hub for scraping or wiping fluid from the surface of a needle as the needle is withdrawn from a catheter tube.

FIG. 8A shows a wiper 176 made from a liquid impermeable film, such as blown PE film, comprising a generally circular configuration with two cut-outs 178. The cut-outs 178 are sized and shaped to permit assembly to a valve opener and are incorporated along a perimeter of the wiper. Thus, the cut-out shape and the wiper's overall configuration may vary depending on the mounting surface of the valve opener. In one exemplary embodiment, the wiper 176 has a solid center section (i.e., no center opening) configured for puncturing by a needle during assembly, as further discussed below.

FIG. 8B is a perspective view of a valve opener 180 provided in accordance with aspects of the present invention. In one exemplary embodiment, the valve opener comprises an actuating end 182 and two legs 184 connected to and extend proximally of the actuating end. Like the valve opener 48 shown in FIG. 3, the actuating end 182 comprises a frusto-conical configuration and incorporates barbs (not shown in FIG. 8B) and a passage for accommodating a needle. In one specific aspect of the present invention, the passage is funnel-like in shape. The two legs 184, while shown extended parallel and offset to an axis defined by the center of the passage, may be angled radially outwardly as they extend proximally. The two legs may also incorporate a slight arc or bend, such as that shown in FIG. 3.

In one exemplary embodiment, a proximally facing wall surface 186 on the actuating end is provided and serves as a mounting surface for a wiper. The wiper 176 of FIG. 8A may be attached to the mounting surface 186 with the cut-outs 178 aligned to the two legs 184. The wiper can be welded to the mounting surface or glued thereto with an appropriate adhesive, such cyanoacrylate or UV cure adhesive. In practice, the valve opener 180 and wiper 176 may be installed as shown in FIG. 8C and when a needle 16 is inserted, the needle tip 72 penetrates the wiper and the wiper subsequently provides a wiping function for the needle. When the wiper 176 is penetrated by the needle tip 72, the needle 16 will open and dilate the wiper putting the needle in a close contact relationship with the wiper 176. Thus, when an upstream section 146 of the needle 16 (i.e., upstream of the wiper) is exposed to blood from blood flashback and is subsequently withdrawn proximally (i.e., to the right of FIG. 5C) to remove the needle 16, the close contact relationship between the wiper 176 and the needle 16 allows the wiper to wipe blood deposits from the needle as the needle is being withdrawn. Consequently, when the needle 16 is fully retracted from the valve opener 180, the needle will appear clean, or at least for the most part visually blood-free, and the tip protector that surrounds the needle tip will likely remain visually blood-free.

FIG. 9A shows a wiper 116 having a generally circular configuration of a first wiper material 122, which may be a microporous plastic film membrane filter, surrounding a plastic inner layer 124, such as a polyethylene (PE) blown film layer. The outer wiper material 122 is preferably air permeable to permit blood flashback. The membrane may be made from PP (polypropylene) or PA (polyamide or Nylon®) spun bound fibers, such as those known in the art from flashback plugs. In a preferred embodiment, the inner layer 124 is plastic film configured for puncturing by a needle when assembling the combination needle hub and needle to a catheter hub, such as the one shown in FIG. 3 having a wiper attached to the valve opener. The wiper should be sufficiently thin so as to not damage the needle tip when the same is passed therethrough. The inner and outer layers can be welded to another.

Figure 9B:
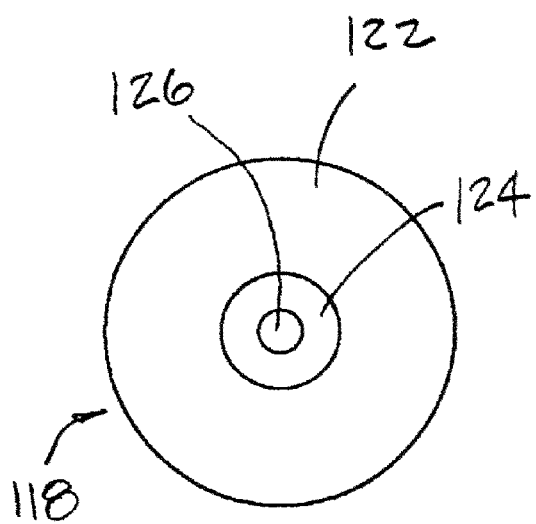
FIG. 9B is a plan view of a second alternative wiper provided in accordance with aspects of the present invention.

In one exemplary embodiment, the wiper 118 shown in FIG. 9B is identical to the wiper 116 shown in FIG. 9A with the exception of a pre-formed opening 126. The opening 126 is preferably sized the same as a needle diameter. In other words, the opening is sized with a zero clearance around the outside diameter of the needle. More preferably, the opening 126 is sized the same as the inside diameter of a catheter tip, which is slightly smaller than the outside diameter of the needle.

Figure 9C:
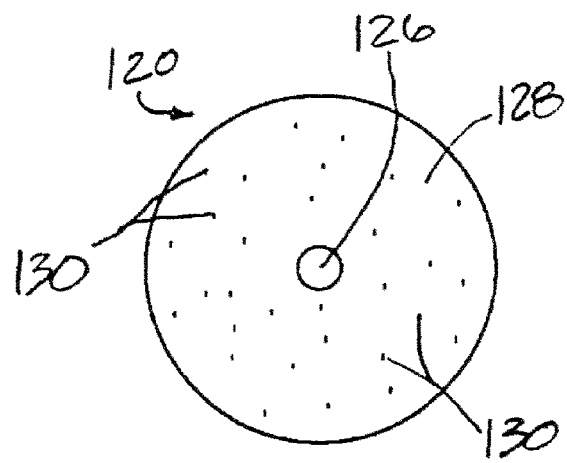
FIG. 9C is a plan view of a third alternative wiper provided in accordance with aspects of the present invention.

FIG. 9C shows yet another wiper embodiment 120 provided in accordance with aspects of the present invention. In one exemplary embodiment, the wiper comprises a single membrane layer 128 having an opening 126, which has a same diameter size as the inside diameter of a catheter tip. A plurality of micro-holes are formed in the membrane layer 128 for venting air. The holes are each sized about 3 μm (micro-meter) to about 8 μm. The membrane may be made from PE, or spun bound PA or PP.

FIG. 9D is a cross-sectional side view of an alternative safety IV catheter assembly provided in accordance with aspects of the present invention, which is generally designated 188. The catheter assembly 188 is similar to the catheter assembly 44 of FIG. 3 and includes a catheter tube 12 and hub 14, a needle 16 and needle hub 18, a tip protector 50, a valve opener 48, and a valve 46. However, in the alternative safety IV catheter assembly 188, an air permeable fluid impermeable wiper 190 is incorporated distal of the valve 46. In one exemplary embodiment, the wiper 190 may be one of the wipers 116, 118 or 120 shown in FIG. 9A, 9B, or 9C and may be attached to a tube bushing 192 for retaining the catheter tube 12 to the catheter hub 14. The tube bushing 192 is preferably made from a thermoplastic material to facilitate attaching the wiper 90 thereon, such as by adhesive or welding. In an alternative embodiment (not shown), a shoulder or seat may be provided within the interior cavity of the catheter hub 14 for accommodating the wiper 190.

Figure 10A:
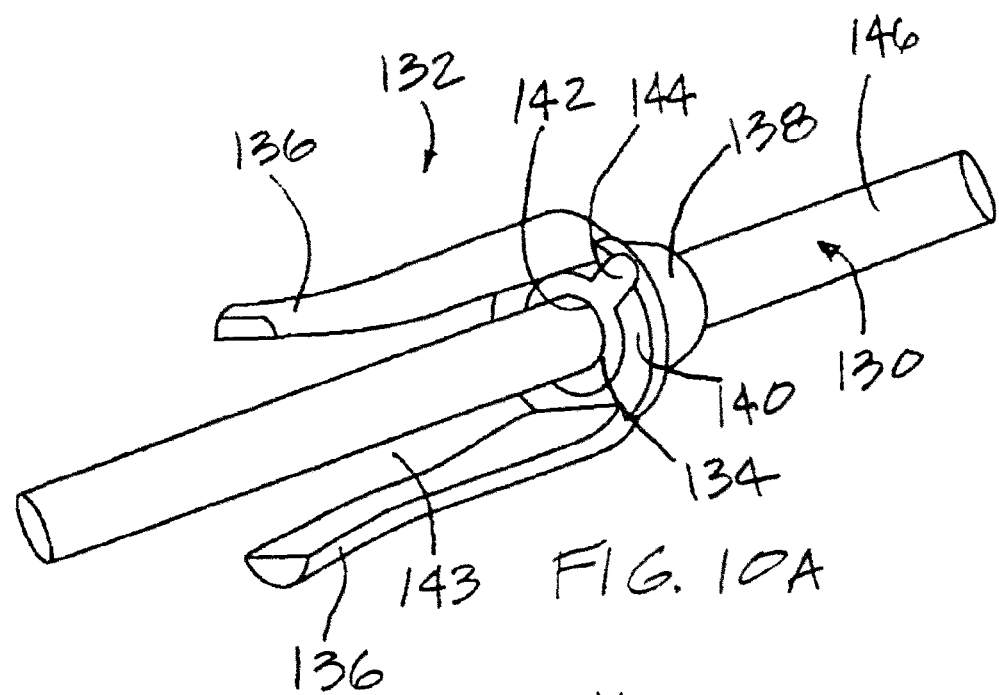
FIG. 10A is a perspective view of a needle projecting through a valve opener having a wiper attached thereto for wiping the needle.

FIG. 10A is a partial perspective view of a needle 130 projecting through a valve opener 132 having a wiper 134 attached thereto. The valve opener 132 is similar to the valve opener shown and described with reference to FIGS. 3-5. FIG. 10A, as well as FIGS. 10B-12 discussed further below, may be viewed as a safety catheter assembly, such as the assembly of FIG. 3, shown without a catheter hub, a needle hub, or a tip protector for clarity and for purposes of discussing only the functions of the wiper. Accordingly, it should be understood that the components shown in FIG. 10A, as well as those in FIGS. 10B-12, are adapted for use with a catheter hub, needle hub, and tip protector in the same manner as those described with reference to FIGS. 1-5. Furthermore, the tip protector is not limited to those shown but also includes those expressly incorporated herein by reference.

In one exemplary embodiment, the valve opener 132 comprises two legs 136 extending proximally of a frusto-conical shape actuating end 138. Although not shown, the actuating end 138 may comprise an undulating surface or barbs for gripping engagement with a hemostatic valve. The actuating end 138 comprises a generally planar proximally facing surface 140 and a passage or lumen 142 for receiving the needle 130. The two legs are radially spaced apart from the needle 130 and has a gap 143 therebetween for accommodating a tip protector.

Figure 10B:
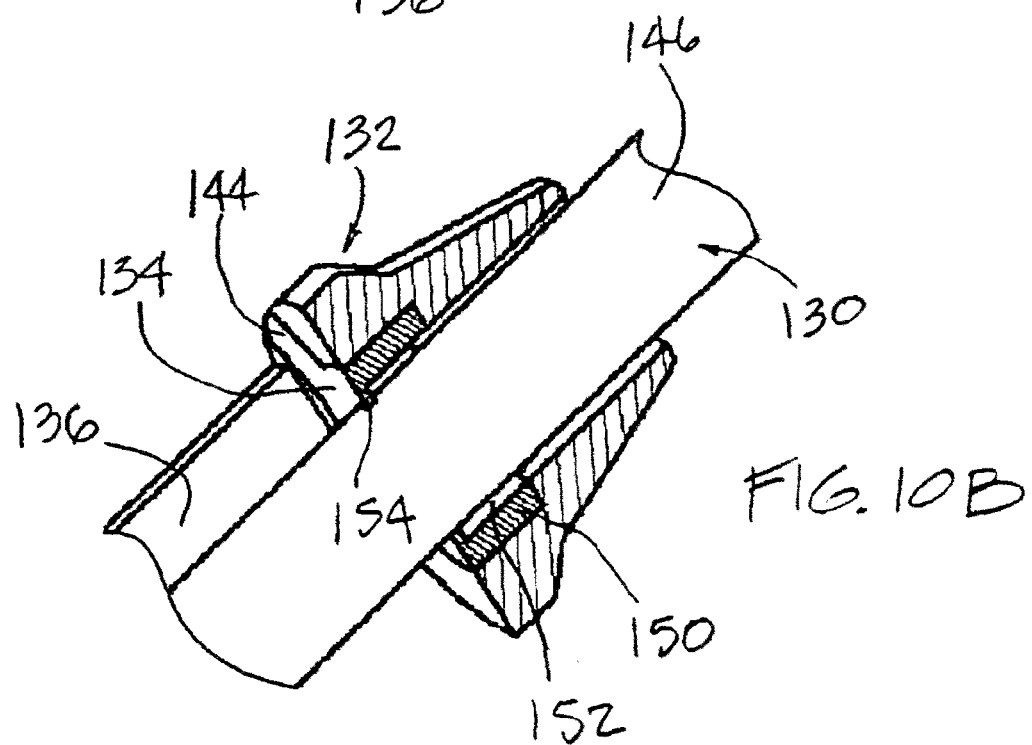
FIG. 10B is a partial perspective and cross-sectional view of the valve opener of FIG. 10A.

FIG. 10B is a partial perspective partial cross-sectional rotated and magnified view of the valve opener 132 of FIG. 10A. The valve opener 132 is shown with the wiper 134 having a ring or cylinder seated within a recessed section of the actuating end 138. The wiper 134 may be insert molded into the opener 132. The tab 144 is the material left between the wiping ring and the cavity gate. Alternatively the wiper can be integral with the actuating end 138. The wiper 134 comprises a passage 152 having a first diameter that is slightly larger than the outside diameter of the needle 130 and a lip 154 having a second diameter, which is preferably the size of the inside diameter of a catheter tip of a catheter tube, that the needle 130 is configured to position in. As discussed above with reference to FIGS. 8C and 9D, when the needle 130 is withdrawn proximally, blood deposits along the upstream end (distal) 146 of the needle is wiped off by the wiper 150.

FIG. 10B shows the valve opener 132 having a single leg 136. However, a valve opener with two legs having a gap therebetween is more preferred. The gap between the two legs 136 is configured to accommodate a tip protector 50, such as that shown in FIGS. 3 and 9D.

Figure 11:
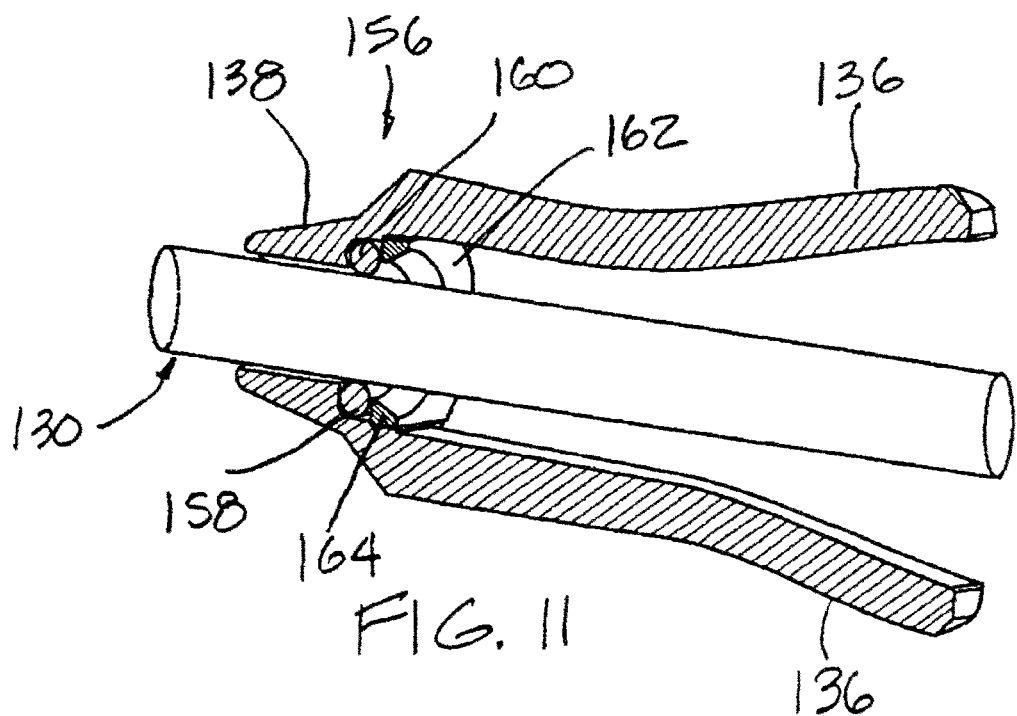
FIG. 11 is a partial perspective and cross-sectional view of an alternative valve opener having, a needle passing therethrough and a wiper that resembles an O-ring.

FIG. 11 is a partial perspective partial cross-sectional side view of an alternative valve opener 156 provided in accordance with aspects of the present invention. The valve opener 156 is shown with a needle 130 projecting through the actuating end 138. In the embodiment shown, a well or recessed area 158 is incorporated for accommodating a wiper in a form of an O-ring 160, which may be made from an elastomeric or TPE material. The O-ring 160 can be slid into the well 158 and a retaining ring 162 pushed against the O-ring 160 to retain the O-ring therein. The retaining ring 162 is secured to the well 158 using simple interference fit. In an alternative embodiment, the retaining ring 162 is welded to the valve opener.

As before, the O-ring 160 is preferably in a contact relationship with the needle 130 so that it may wipe the needle as the needle is withdrawn proximally (to the right in FIG. 11) away from the opener 156. The opener 156 is shown having a gap between the two legs 136 for accommodating a tip protector (not shown). The opener 156 and the needle 130 are configured to be used with a catheter hub in the same manner as the opener and needle shown in FIG. 3.

Figure 12:
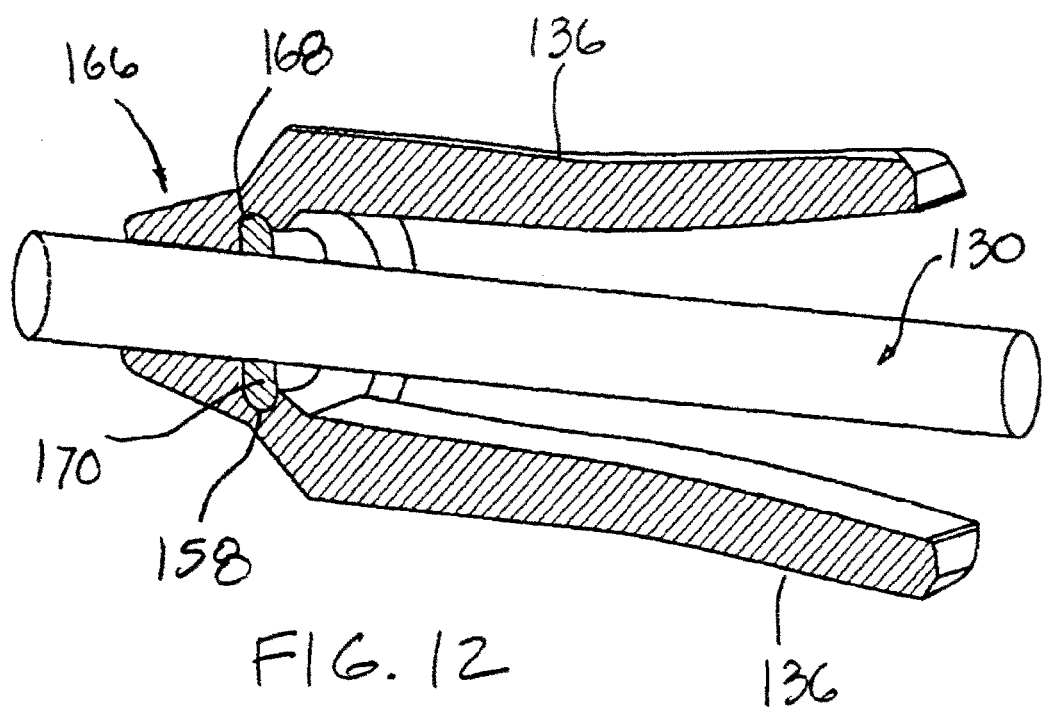
FIG. 12 is a partial perspective and cross-sectional view of an alternative valve opener having a needle passing therethrough and a wiper that is registered to an annular groove.

FIG. 12 is a partial cross-sectional perspective view of yet another alternative valve opener 166 provided in accordance with aspects of the present invention. In the embodiment shown, an annular groove 168 is incorporated in a well 158 for accommodating an elastomeric or TPE wiper 170. The wiper 170 resembles a flattened O-ring, like a doughnut, but may in fact also be an O-ring. This configuration enables a common valve opener to be used with various needle outside and O-ring inside diameters. The wiper 170 is retained within the well 158 without a separate retaining ring, such as the ring 162 in FIG. 11. The wiper 170 may be snapped-fit into the groove 168 during assembling.

Figure 13:
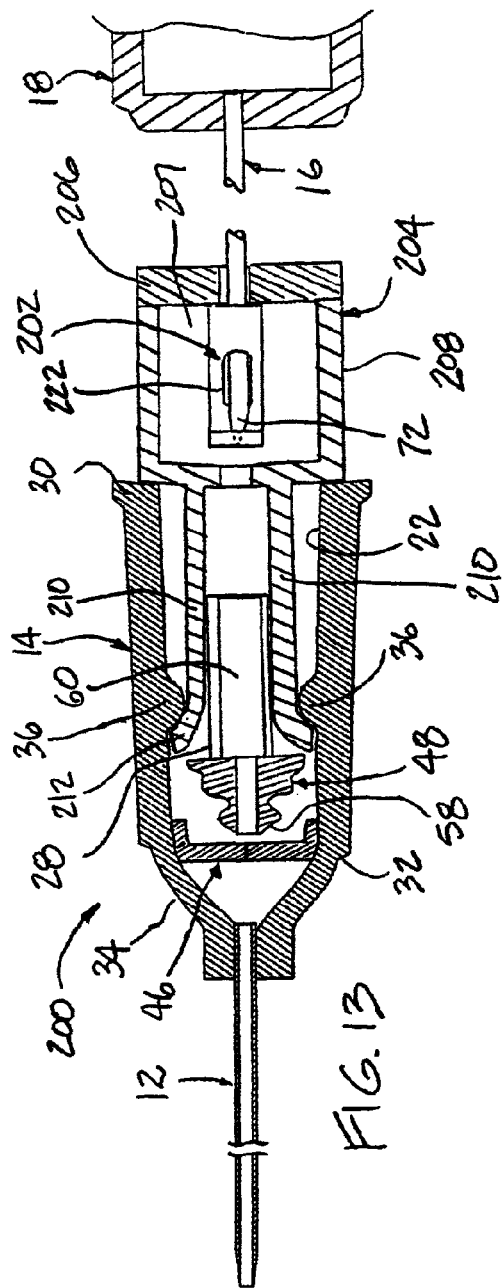
FIG. 13 is a cross-sectional side view of yet another alternative catheter assembly provided in accordance with aspects of the present invention, which includes a third housing positioned between a catheter and a needle hub.

FIG. 13 is a cross-sectional side view of yet another alternative catheter assembly provided in accordance with aspects of the present invention, which is generally designated 200. The catheter assembly 200 incorporates similar components as the assembly shown in FIGS. 8C and 9D, including a catheter tube 12 attached to a catheter hub 14, a needle 16 attached to a needle hub 18, a hemostatic valve 46, a valve opener 48 comprising a pair of legs 60 (only one shown) positioned in corresponding channels 28 in the catheter hub 14, a wiper (not shown) attached to either the catheter huh 14 or the valve opener 48, and a tip protector 202 for blocking the needle tip 72. However, rather than placing the tip protector 202 in a gap defined by the two legs 60 in the valve opener 48, a third housing 204 is incorporated for accommodating the tip protector. Additionally, the wiper (not shown) may be attached to the third housing 204, distal of the tip protector 202, for wiping the needle as the needle is retracted following catheterization.

In one exemplary embodiment, the third housing 204 incorporates a rear plate or panel 206 attached to an enclosed housing section 208 for closing an opening 207 on the enclosed housing section 208. The opening 207 on the enclosed housing section 208 allows the tip protector 202 to be placed therein during assembly. The rear plate 206 may be attached to the housing section 208 using adhesive, welding, or detents. Alternatively, the enclosed housing section 208 may incorporate an opening on a side, orthogonal to the rear plate 206.

The third housing 204 incorporates a pair of arms 210 each comprising a hook 212. The two hooks 212 are configured to engage the two bumps 36 to retain the third housing 204 to the catheter hub 14 in a ready to use position. The two arms 210 are preferably flexible to provide a gripping force against the two bumps 36, which is higher than the frictional force to withdraw the needle through the tip protector 202, hemostatic valve 46, and catheter 12. Alternatively the two arms 210 can be biased radially outward to increase the gripping force. Further, the two arms can be biased inwardly against the needle shaft to decrease the gripping force after the needle is withdrawn proximal of the arms 210.

Figure 14:
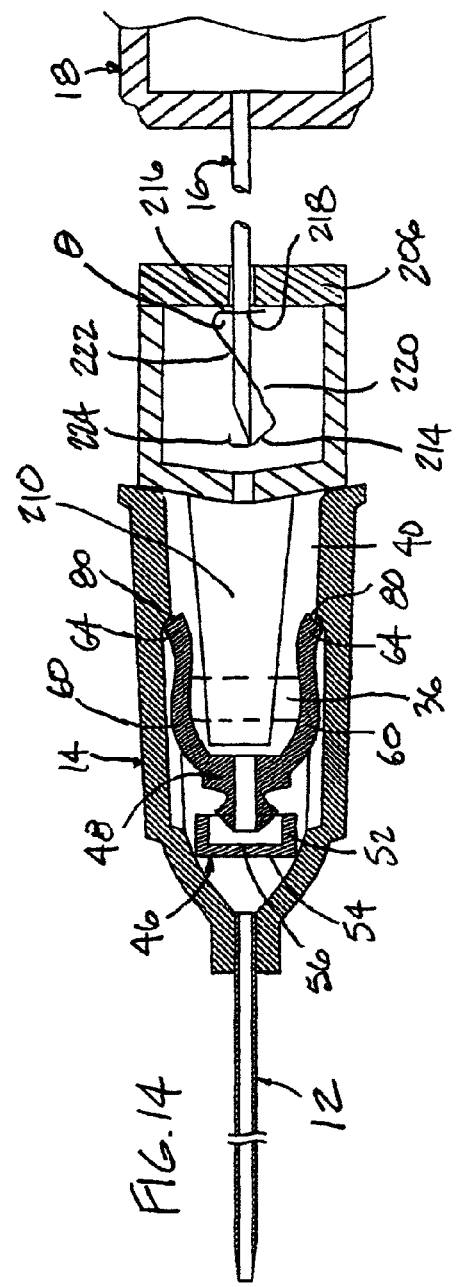
FIG. 14 is a cross-sectional side view of the catheter assembly of FIG. 13 taken along an orthogonal plane.

Following successful catheterization, the needle 16 is retracted proximally away from the catheter tube 12 in the same manner as previously discussed (i.e., to the right of FIGS. 13 and 14). As the needle tip 72 moves proximally of the distal wall 214 of the tip protector 202, the tip protector 202 engages the needle 16 and further proximal movement of the needle 16 causes the tip protector 202 to pull on the rear plate 206 of the third housing 204, which then disengages the two hooks 212 from the two bumps 36. Thus, the gripping force between the two hooks 212 and the two bumps 36 should be less than the gripping force between the tip protector 202 and the needle 16.

Referring now to FIG. 14, the tip protector 202 comprises a proximal wall 216 comprising an opening 218, an arm 220 comprising an opening 222 (FIG. 13), and a distal wall 214 at a distal end of the arm 220. The proximal wall 216 and the arm 220 define an angle $\Theta$ therebetween. In a ready to use position (not shown), the end edge 224 of the tip protector 202 is biased against the side of the needle 16 and the angle $\Theta$ has a ready angle value $\Theta_{ready}$. When in the activated position (FIGS. 13 and 14), the angle $\Theta$ increases to a protected angle value $\Theta_{protected}$, which is larger than the ready angle value $\Theta_{ready}$. When this occurs, the arm is further canted and the opening 222 on the arm grips the needle to engage the needle without a crimp.

Although limited catheter assembly embodiments and their components have been specifically described and illustrated, many modifications, combinations, and variations will be apparent to those skilled in the art. For example, the length, size, colors, and appearance of the needle hub and catheter hub may be modified, a tip protector other than those specifically incorporated herein may be use, and rather than two equally long legs on a valve opener, a single leg or two legs with dissimilar lengths may be use. Additionally, rather than placing a tip protector in the catheter hub for blocking the needle tip, a third housing may be incorporated to house the tip protector and the third housing positioned between the catheter hub and the needle hub as described in U.S. application Ser. No. 10/109,797, entitled "SAFETY SPRING CATHETER INTRODUCER ASSEMBLY," filed Mar. 29, 2002, the contents of which are expressly incorporated herein by reference as if set forth in full. The third housing and tip protector may also be configured as described in U.S. application Ser. No. 10/468,923 entitled "NEEDLE ASSEMBLY WITH PROTECTIVE ELEMENT," and in U.S. Pat. No. 7,125,397, the contents of which are expressly incorporated herein by reference. Furthermore, it is understood and contemplated that features specifically discussed for one valve embodiment, wiper, valve opener, or tip protector may be adopted for inclusion with another valve embodiment provided the functions are compatible. For example, the needle and tip protector of FIG. 6, the valve opener and wiper of FIG. 10A, and the hemostatic valve of FIG. 8C may be use with the catheter hub of FIG. 2, even though the overall combination was not expressly discussed. Accordingly, it is to be understood that the catheter assemblies and their components constructed according to principles of this invention may be embodied other than as specifically described herein. The invention is also defined in the following claims.

What is claimed is:

1. A method of wiping blood from a needle during a process of emplacing a catheter using a catheter assembly, the method comprising:

puncturing a person's vasculature with a sharp distal tip of the needle of the catheter assembly, the needle extending distally from a first hub including a housing having an exterior surface and an interior surface defining an interior cavity;

penetrating the vasculature with the catheter of the catheter assembly, the catheter being disposed about the needle and extending distally from a second hub including a housing having an exterior surface and an interior surface defining an interior cavity, the first and second hubs releasably engaging one another;

withdrawing the needle from the vasculature while maintaining the catheter within the vasculature by disengaging the first hub from the second hub and moving the first hub proximally relative to the second hub, the proximal movement causing the needle to withdraw from the catheter; and wiping blood from the needle as it withdraws by passing the needle through a wiper, the wiper being disposed in the second hub and having a fixed continuous perimeter defining an opening, the fixed continuous perimeter being in contact with the needle along a section of the fixed continuous perimeter from a point on the needle inside the interior cavity of the second hub and continuously contacting the needle during the withdrawing step to at least a point adjacent the sharp distal tip for wiping the needle during the withdrawing step.

2. The method of claim 1, wherein the wiper is attached directly or indirectly to the second hub so that the wiper remains stationary as the needle is withdrawn.

3. The method of claim 1, wherein as the needle is withdrawn it passes through a hemostatic valve and a valve opener, both of which are positioned in the interior cavity of the second hub.

4. The method of claim 3, wherein the wiper is attached to the valve opener.

5. The method of claim 1, wherein as the needle is withdrawn it passes through a tip protector positioned in the interior cavity of the second hub.

6. The method of claim 5, wherein the tip protector comprises two arms that intersect.

7. The method of claim 5, wherein the tip protector comprises a first protector body surrounded by a second protector body.

8. The method of claim 5, wherein tip protector comprises two arms that extend, at least in part, to one side of the needle.

9. The method of claim 1, wherein the wiper is liquid impermeable.

10. The method of claim 1, wherein the wiper is an O-ring.

11. A method of cleaning an exterior of a needle during a process of emplacing a catheter using a catheter assembly, the method comprising;
    inserting the needle of the catheter assembly into a person's vasculature at an access site, the needle having a sharp distal tip and extending distally from a proximal hub;
    inserting the catheter of the catheter assembly into the vasculature at the access site, the catheter being disposed about the needle and extending distally from a distal hub including a housing having an exterior surface and an interior surface defining an interior cavity, the proximal and distal hubs releasably engaging one another;
    disengaging the proximal hub from the distal hub and moving the proximal hub proximally relative to the distal hub, the proximal movement drawing the needle out of the vasculature and the catheter while the catheter remains within the vasculature; and
    passing the needle through a wiper as it withdraws, the wiper removing blood from the exterior of the needle, the wiper having a fixed continuous perimeter defining an opening, the fixed continuous perimeter being in contact with the exterior of the needle along a section of the fixed continuous perimeter from a point on the needle inside the interior cavity of the distal hub and continuously contacting the needle during the withdrawing step to at least a point adjacent the sharp distal tip for wiping the needle during the withdrawing step.

12. The method of claim 11, wherein the wiper is attached directly or indirectly to the distal hub so that the wiper remains stationary as the needle is withdrawn.

13. The method of claim 11, wherein as the needle is withdrawn it passes through a hemostatic valve and a valve opener, both of which are positioned in an interior cavity of the distal hub.

14. The method of claim 13, wherein the wiper is attached to the valve opener.

15. The method of claim 11, wherein as the needle is withdrawn it passes through a tip protector positioned in an interior cavity of the distal hub.

16. The method of claim 15, wherein the tip protector comprises two arms that intersect.

17. The method of claim 15, wherein the tip protector comprises a first protector body surrounded by a second protector body.

18. The method of claim 15, wherein the tip protector comprises two arms that extend, at least in part, to one side of the needle.

19. The method of claim 11, wherein the wiper is liquid impermeable.

20. The method of claim 11, wherein the wiper is an O-ring.

* * * * *

UNITED STATES PATENT AND TRADEMARK OFFICE
CERTIFICATE OF CORRECTION

PATENT NO. : 8,419,688 B2
APPLICATION NO. : 12/768155
DATED : April 16, 2013
INVENTOR(S) : Kevin Woehr et al.

It is certified that error appears in the above-identified patent and that said Letters Patent is hereby corrected as shown below:

In the Specifications

In column 1, line 59, delete "catherizaton." and insert -- catheterization. --, therefor.

In column 6, line 25, delete "polyoximethylene" and insert -- polyoxymethylene --, therefor.

In the Claims

In column 13, line 20, in claim 8, after "wherein" insert -- the --.

Signed and Sealed this
Seventh Day of January, 2014

Margaret A. Focarino
*Commissioner for Patents of the United States Patent and Trademark Office*